(12) United States Patent
Chang et al.

(10) Patent No.: US 12,383,761 B2
(45) Date of Patent: Aug. 12, 2025

(54) WEARABLE DEVICE FOR PAIN TREATMENT BY COMPOUND PHOTO-CHEMICAL ACTION PRINCIPLE

(71) Applicant: Wellscare Co., Ltd, Suwon-si (KR)

(72) Inventors: Sang-Hyun Chang, Suwon-si (KR); Sung-Won Lee, Yongin-si (KR)

(73) Assignee: Wellscare Co., Ltd, Suwon-si (KR)

( * ) Notice: Subject to any disclaimer, the term of this patent is extended or adjusted under 35 U.S.C. 154(b) by 1003 days.

(21) Appl. No.: 17/439,050

(22) PCT Filed: Jan. 27, 2021

(86) PCT No.: PCT/KR2021/001074
§ 371 (c)(1),
(2) Date: Sep. 14, 2021

(87) PCT Pub. No.: WO2022/158629
PCT Pub. Date: Jul. 28, 2022

(65) Prior Publication Data
US 2022/0233877 A1  Jul. 28, 2022

(30) Foreign Application Priority Data
Jan. 25, 2021  (KR) .................. 10-2021-0010432

(51) Int. Cl.
*A61N 5/067* (2006.01)
*A61N 5/06* (2006.01)

(52) U.S. Cl.
CPC ........... *A61N 5/067* (2021.08); *A61N 5/0616* (2013.01)

(58) Field of Classification Search
CPC ...... A61B 18/20–18/28; A61N 5/06–2005/073
USPC .................... 607/88–94; 606/2–19
See application file for complete search history.

(56) References Cited

U.S. PATENT DOCUMENTS

2008/0319507 A1* 12/2008 Myers .................. A61N 1/40
607/59
2015/0112411 A1* 4/2015 Beckman ............. A61N 5/0616
607/90

(Continued)

FOREIGN PATENT DOCUMENTS

CN          1233968 A    * 11/1999  ........... A61B 8/0875
JP      2019504692 A       2/2019

(Continued)

OTHER PUBLICATIONS

Kimura, Tatsuo, "Notice of Reasons for Refusal," Japanese Office Action, Apr. 20, 2023.

*Primary Examiner* — Benjamin J Klein
*Assistant Examiner* — Vynn V Huh
(74) *Attorney, Agent, or Firm* — Bridgeway IP Law Group, PLLC; Sang Ho Lee; Hyun Woo Shin

(57) ABSTRACT

Disclosed is a body-wearable apparatus for treating pain by a principle of complex photo-biochemical actions. According to one aspect of the present invention, there is provided the body-wearable apparatus for treating pain by a principle of complex photo-biochemical actions including a body portion in which a plurality of transmission holes are formed so that light is transmitted therethrough, a circuit board disposed inside the body portion, a built-in battery disposed inside the body portion, a first light irradiating portion electrically connected to the circuit board and configured to irradiate blue light-emitting diode (LED) light through the transmission holes of the body portion, and a second light irradiating portion electrically connected to the circuit board and configured to irradiate low-level laser light through the transmission holes of the body portion, wherein each of the first and second light irradiating portions is provided to cause at least two or more photo-biochemical reactions among cell activation, cell regeneration, cell division, blood (Continued)

flow improvement, vasodilation, cell degradation, and nerve stimulation on tissue in a body part to be treated through simultaneous or alternate light output.

10 Claims, 9 Drawing Sheets

(56) References Cited

U.S. PATENT DOCUMENTS

| | | | | |
|---|---|---|---|---|
| 2015/0177423 A1* | 6/2015 | Scipioni | ............... | A41D 13/005 |
| | | | | 428/221 |
| 2016/0050723 A1* | 2/2016 | Gochnauer | ............ | H05B 45/22 |
| | | | | 315/307 |
| 2019/0159838 A1 | 5/2019 | Boutoussov et al. | | |

FOREIGN PATENT DOCUMENTS

| | | | | |
|---|---|---|---|---|
| JP | 2019525792 A | | 9/2019 | |
| JP | 2020130994 A | * | 8/2020 | |
| JP | 2020532372 A | | 11/2020 | |
| KR | 20-0412781 Y1 | | 3/2006 | |
| KR | 10-1006764 B1 | | 1/2011 | |
| KR | 10-2014-0047705 A | | 4/2014 | |
| KR | 10-2019-0100655 A | | 8/2019 | |
| KR | 10-2019-0103532 A | | 9/2019 | |
| KR | 10-2020-0020106 A | | 2/2020 | |
| KR | 10-2079094 B1 | | 2/2020 | |
| KR | 10-2108677 B1 | | 5/2020 | |
| WO | WO-2009066816 A1 | * | 5/2009 | ............. A61H 11/00 |
| WO | WO-2013036558 A1 | * | 3/2013 | ........... A61F 9/0079 |

* cited by examiner

WEARABLE DEVICE FOR PAIN TREATMENT BY COMPOUND PHOTO-CHEMICAL ACTION PRINCIPLE

TECHNICAL FIELD

The present invention relates to a body-wearable apparatus for treating pain by a principle of complex photo-biochemical actions.

NATIONAL RESEARCH AND DEVELOPMENT PROJECT THAT SUPPORTS THIS INVENTION

[Project identification number] 1920007
[Project number] D1920007
[Department name] Gyeonggi-do
[Project management (specialty) organization name] Gyeonggi Business & Science Accelerator
[Research Project Name]
  [Title of project] Development of a pain treatment device, which combines intermittent ultrasound technology and cold laser technology and is capable of simultaneously treating superficial and deep muscles for acute pain, a pain platform in which pain management may be customized.
  [Contribution rate] 1/1
  [Project execution organization name] WellsCare Co.,Ltd
  [Research period] Feb. 1, 2020-Jan. 31, 2021

BACKGROUND ART

Low-level lasers (LLLs) are known through various clinical data to cause various effects such as pain relief, blood flow improvement, blood flow enhancement, skin regeneration, cell activation, fat reduction, and cell stimulation depending on a specific wavelength range. Compared to high-level lasers used for the purpose of destruction or intentional damage or necrosis of skin tissue, the low-level laser, which has a wavelength band of 600 nm or more with a relatively low output of 100 mW or less, is relatively safe and has effects of promoting metabolism, revitalizing cells, and increasing immunity and thus has a function of recovering damaged cell tissue. In particular, when the low-level laser having a wavelength band of 800 nm or more is selectively irradiated on acupoints, it is known to have a function of relieving pain in skin or muscle and promoting the healing of an affected region by achieving the same effect as acupuncture or moxibustion treatment.

PRIOR ART DOCUMENT

Patent Document

Korean Patent Application Publication No. 10-1006764 (publication date: Jun. 23, 2015)

DISCLOSURE

Technical Problem

The present invention is directed to providing a body-wearable apparatus for treating pain by a principle of complex photo-biochemical actions, which is capable of causing two or more photo-biochemical reactions in a treatment site using light-emitting diode (LED) light and low-level laser light.

Technical Solution

According to one aspect of the present invention, there is provided a body-wearable apparatus for treating pain by a principle of complex photo-biochemical actions, the apparatus including a body portion in which a plurality of transmission holes are formed so that light is transmitted therethrough, a circuit board disposed inside the body portion, a built-in battery disposed inside the body portion, a first light irradiating portion electrically connected to the circuit board and configured to irradiate blue light-emitting diode (LED) light through the transmission holes of the body portion, and a second light irradiating portion electrically connected to the circuit board and configured to irradiate low-level laser light through the transmission holes of the body portion, wherein each of the first and second light irradiating portions is provided to cause at least two or more photo-biochemical reactions among cell activation, cell regeneration, cell division, blood flow improvement, vasodilation, cell degradation, and nerve stimulation on tissue in a body part to be treated through simultaneous or alternate light output.

The first light irradiating portion may include at least one blue LED element that has a wavelength range of 440 nm to 460 nm and is configured to suppress a pain-inducing factor by improving a supply of oxygen and nutrients to a muscle in a light irradiated region by a principle of promoting generation and circulation of nitric oxide (NO).

The second light irradiating portion may include a first element having a wavelength range of 630 nm to 680 nm, a second element having a wavelength range of 800 nm to 850 nm, and a third element having a wavelength range of 900 nm to 920 nm, wherein the first element may be used for a purpose of relieving pain in a treatment site, the second element may be used for a purpose of cell regeneration or cell activation in the treatment site, the third element may be used for a purpose of nerve stimulation in the treatment site, and at least two elements among the first to third elements may operate simultaneously.

The apparatus may further include an ultrasonic element provided in the body portion and controlled to simultaneously or alternately generate at least one ultrasonic energy of 1 MHz and 3 MHz toward a body.

At least two of the first light irradiating portion, the second light irradiating portion, and the ultrasonic element may be controlled to simultaneously emit light.

The apparatus may further include an ultrasonic element provided in the body portion and controlled to simultaneously or alternately generate ultrasonic energy for treatment of superficial muscle and ultrasonic energy for treatment of deep muscle.

At least two of the first light irradiating portion, the second light irradiating portion, and the ultrasonic element may be controlled to simultaneously emit light.

The body portion may further include a heating portion configured to provide thermal energy to a treatment site for thermal treatment.

The heating portion may include a heat sink provided to absorb heat from the second light irradiating portion, a heating element configured to heat the heat sink, a temperature sensor configured to sense a temperature of the heat sink, and a controller configured to control the heating element according to the temperature of the heat sink by detecting a temperature signal from the temperature sensor.

The apparatus may further include a biometric signal detection sensor installed in the body portion and configured to detect a biometric signal of a user in order to control an operation mode of the light irradiating portion.

Advantageous Effects

According to the present invention, two or more photo-biochemical reactions can be caused in a treatment site using light-emitting diode (LED) light and low-level laser light.

DESCRIPTION OF REFERENCE NUMERALS

Figure 1:
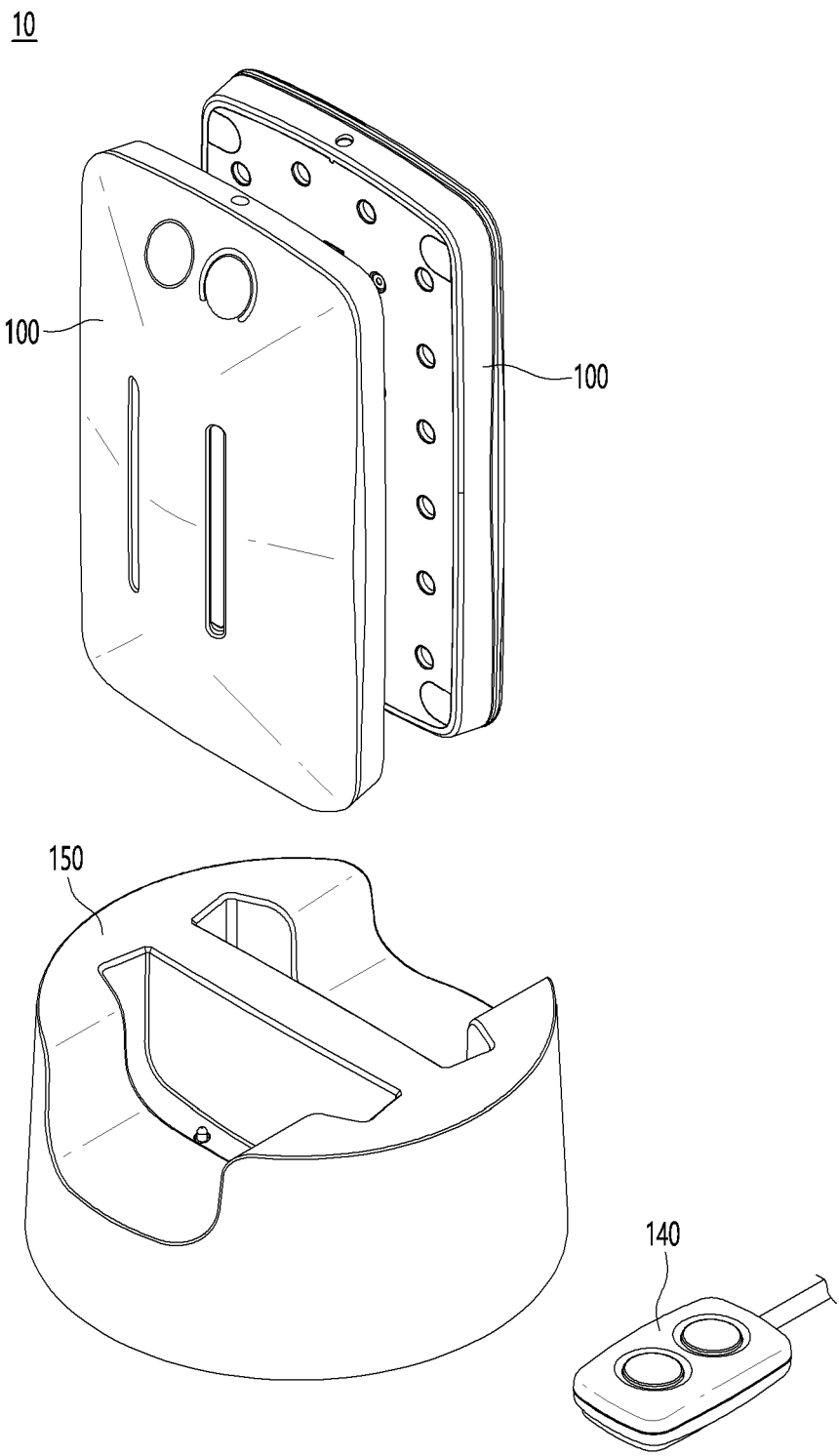
FIG. 1 is a view illustrating a body-wearable apparatus set for treating pain by a principle of complex photo-biochemical actions, a cradle, and a remote controller according to one embodiment of the present invention.

10: body-wearable apparatus set for treating pain by a principle of complex photo-biochemical actions
20: peripheral region
30: central region
40: band
100: body-wearable apparatus for treating pain by a principle of complex photo-biochemical actions
110: body portion
111: first light irradiating portion
112: blue LED
113: second light irradiating portion
114: first element
116: second element
118: third element
119: ultrasonic element
119*a*: first ultrasonic element
119*b*: second ultrasonic element
120: biometric signal detection sensor
121: oscillator
122: circuit board
124: built-in battery
126: battery housing
130: heating portion
132: heating element
134: heat sink
135: insertion hole
136: control button portion
140: remote controller
150: cradle

MODES OF THE INVENTION

The present invention may be modified in various forms and have various embodiments, and thus particular embodiments thereof will be illustrated in the accompanying drawings and described in the detailed description. It should be understood, however, that there is no intent to limit the present invention to the particular forms disclosed, but on the contrary, the present invention is to cover particular modifications, equivalents, and alternatives falling within the spirit and scope of the present invention. In describing the present invention, detailed descriptions of well-known technologies will be omitted when it is determined that they may obscure the gist of the present invention.

It should be understood that, although the terms "first," "second," and the like may be used herein to describe various components, these components should not be limited by these terms. The terms are used only for the purpose of distinguishing one component from another component.

The terms used herein are for the purpose of describing particular exemplary embodiments only and are not intended to be limiting to the present invention. A singular expression includes a plural expression unless the context clearly indicates otherwise. In the present application, it will be further understood that the terms "comprise," "comprising," "include," and/or "including," when used in this specification, specify the presence of stated features, integers, steps, operations, components, parts and/or groups thereof but do not preclude the presence or addition of one or more other features, integers, steps, operations, components, parts and/or groups thereof.

Hereinafter, embodiments of a body-wearable apparatus 100 for treating pain by a principle of complex photo-biochemical actions and a body-wearable apparatus set 10 for treating pain by a principle of complex photo-biochemical actions, and a method of controlling the same according to the present invention will be described in detail with reference to the accompanying drawings, and in this case, the same or corresponding elements will be given the same reference numbers regardless of drawing symbols, and redundant descriptions will be omitted.

According to the present embodiment, as shown in FIGS. 1 to 6B, there is provided the body-wearable apparatus 100 for treating pain by a principle of complex photo-biochemical actions, which includes a body portion 110, in which a plurality of transmission holes are formed so that light is transmitted therethrough, a circuit board 122 disposed inside the body portion 110, a built-in battery 124 disposed inside the body portion 110, a first light irradiating portion 111 electrically connected to the circuit board 122 and configured to irradiate light-emitting diode (LED) light through the transmission holes of the body portion 110, and a second light irradiating portion 113 electrically connected to the circuit board 122 and configured to irradiate low-level laser light through the transmission holes of the body portion 110, wherein the second light irradiating portion 113 includes a plurality of laser elements that irradiate low-level laser light of different wavelength bands to a treatment site for two or more photo-biochemical reactions, and the photo-biochemical reactions include at least one of cell activation, cell regeneration, cell division, blood flow improvement, vasodilation, cell degradation, and nerve stimulation.

Hereinafter, each component of the body-wearable apparatus for treating pain by a principle of complex photo-biochemical actions according to the present embodiment will be described with reference to FIGS. 1 to 5.

Figure 2:
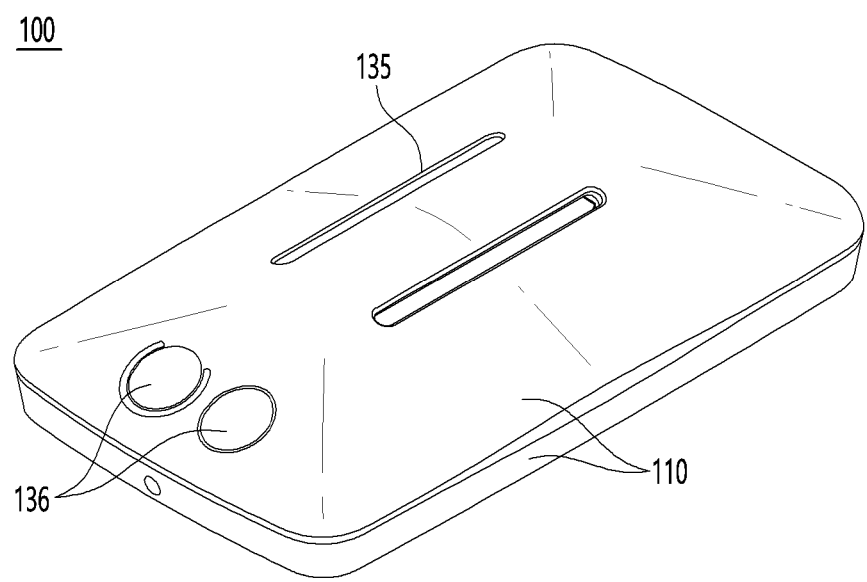
FIG. 2 is a perspective view illustrating a body-wearable apparatus for treating pain by a principle of complex photo-biochemical actions according to one embodiment of the present invention.
Figure 3:
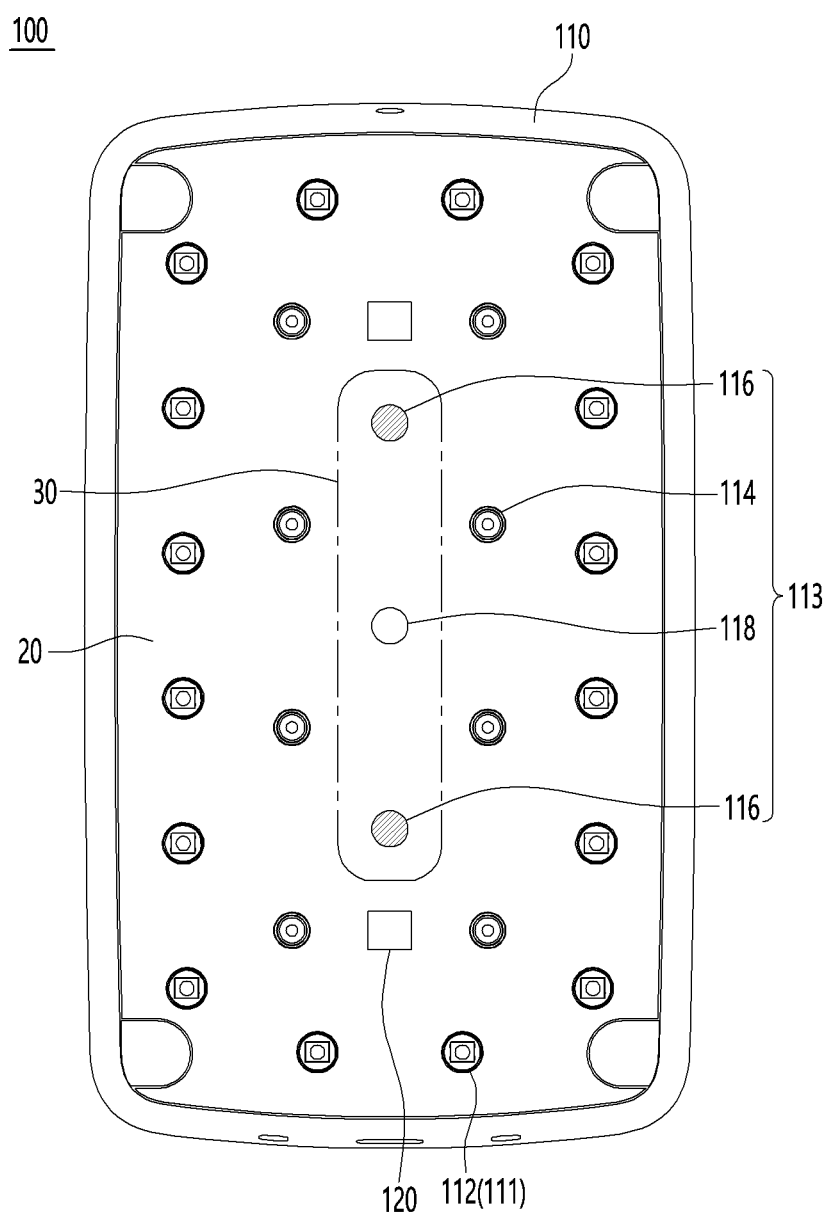
FIG. 3 is a rear view illustrating the body-wearable apparatus for treating pain by a principle of complex photo-biochemical actions according to one embodiment of the present invention.

As shown in FIGS. 2 and 3, the body portion 110 has a plate shape and may be easily attached to a treatment site. The plurality of transmission holes may be formed in one surface of the body portion 110 so that light is transmitted therethrough.

Insertion holes 135 may be formed in the other surface of the body portion 110 so that a band 40 is inserted therethrough. The body portion 110 may be disposed to correspond to the treatment site by inserting the band 40 through the insertion holes 135 and may be stably seated as the band 40 is fixed to a body of a user.

In addition, a control button portion 136 through which a power supply and an operation mode may be controlled may be formed on the body portion 110.

Figure 4:
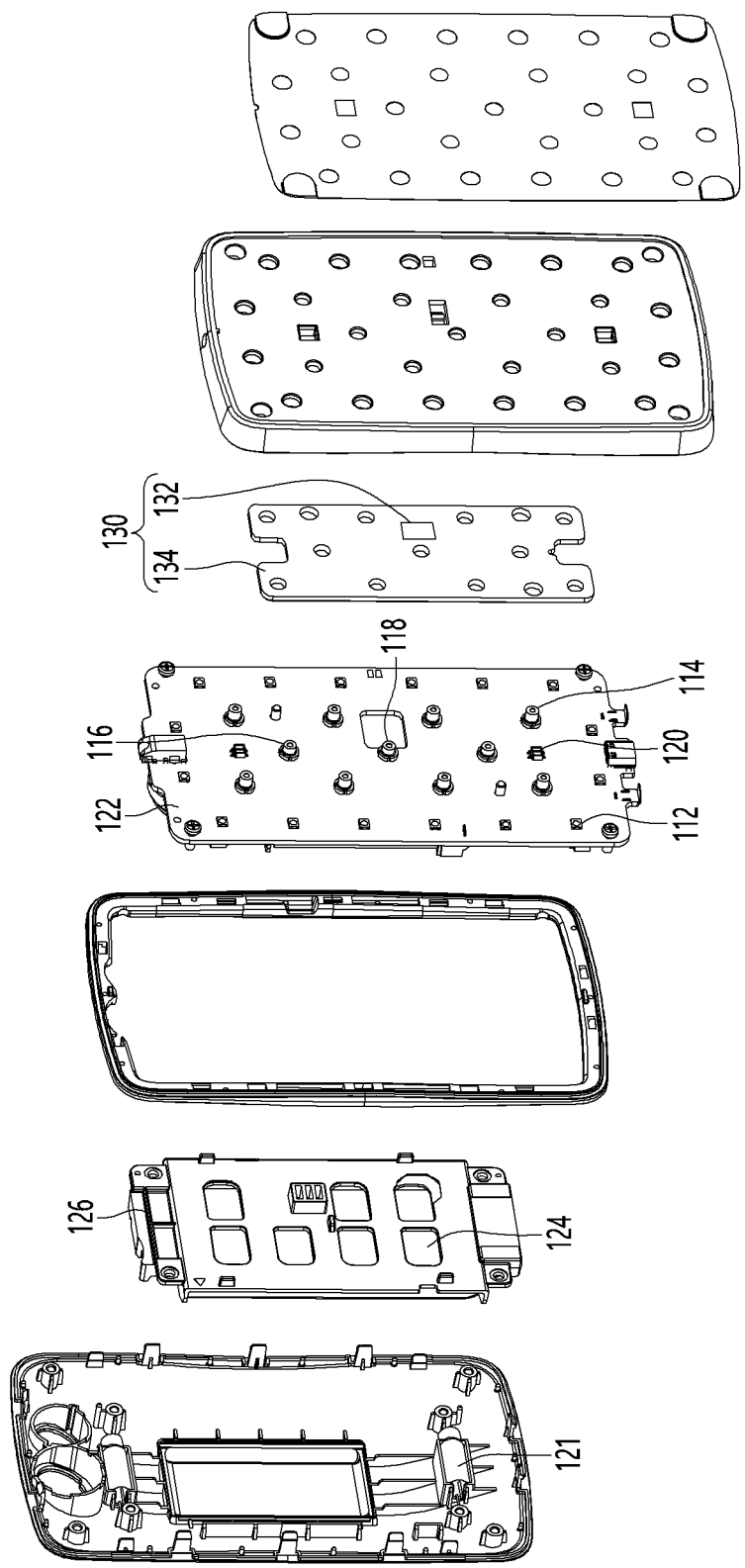
FIG. 4 is an exploded view illustrating the body-wearable apparatus for treating pain by a principle of complex photo-biochemical actions according to one embodiment of the present invention.
Figure 5:
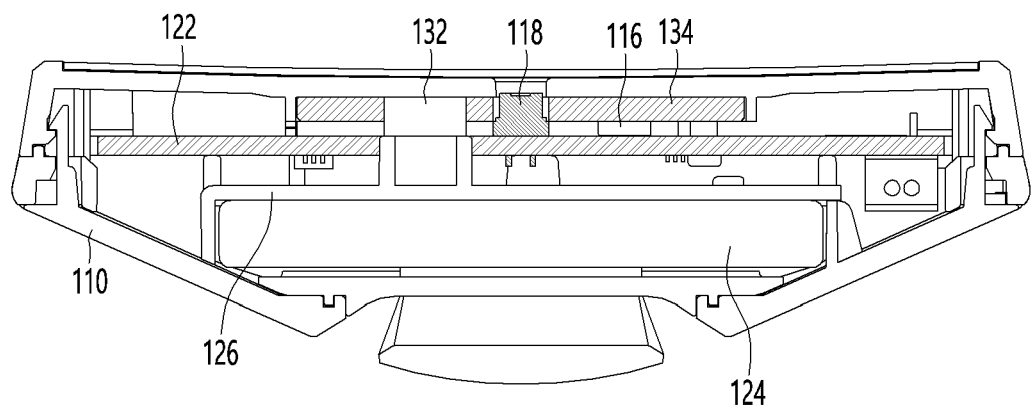
FIG. 5 is a cross-sectional view illustrating an internal configuration of the body-wearable apparatus for treating pain by a principle of complex photo-biochemical actions according to one embodiment of the present invention.
Figure 6A:
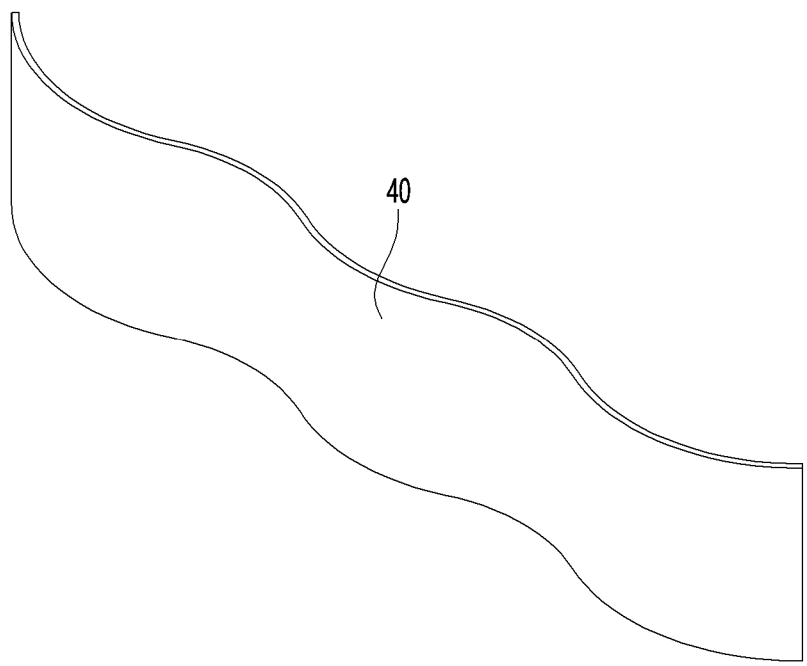
FIGS. 6A and 6B are views illustrating a band member for attaching the body-wearable apparatus for treating pain by a principle of complex photo-biochemical actions according to one embodiment of the present invention to a human body.
Figure 6B:
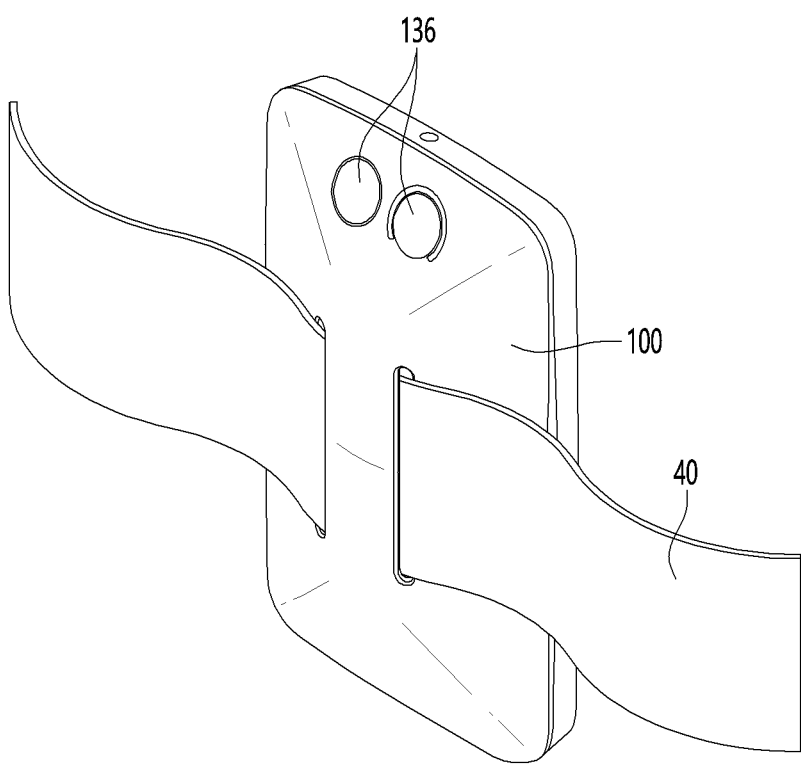
Figure 7:
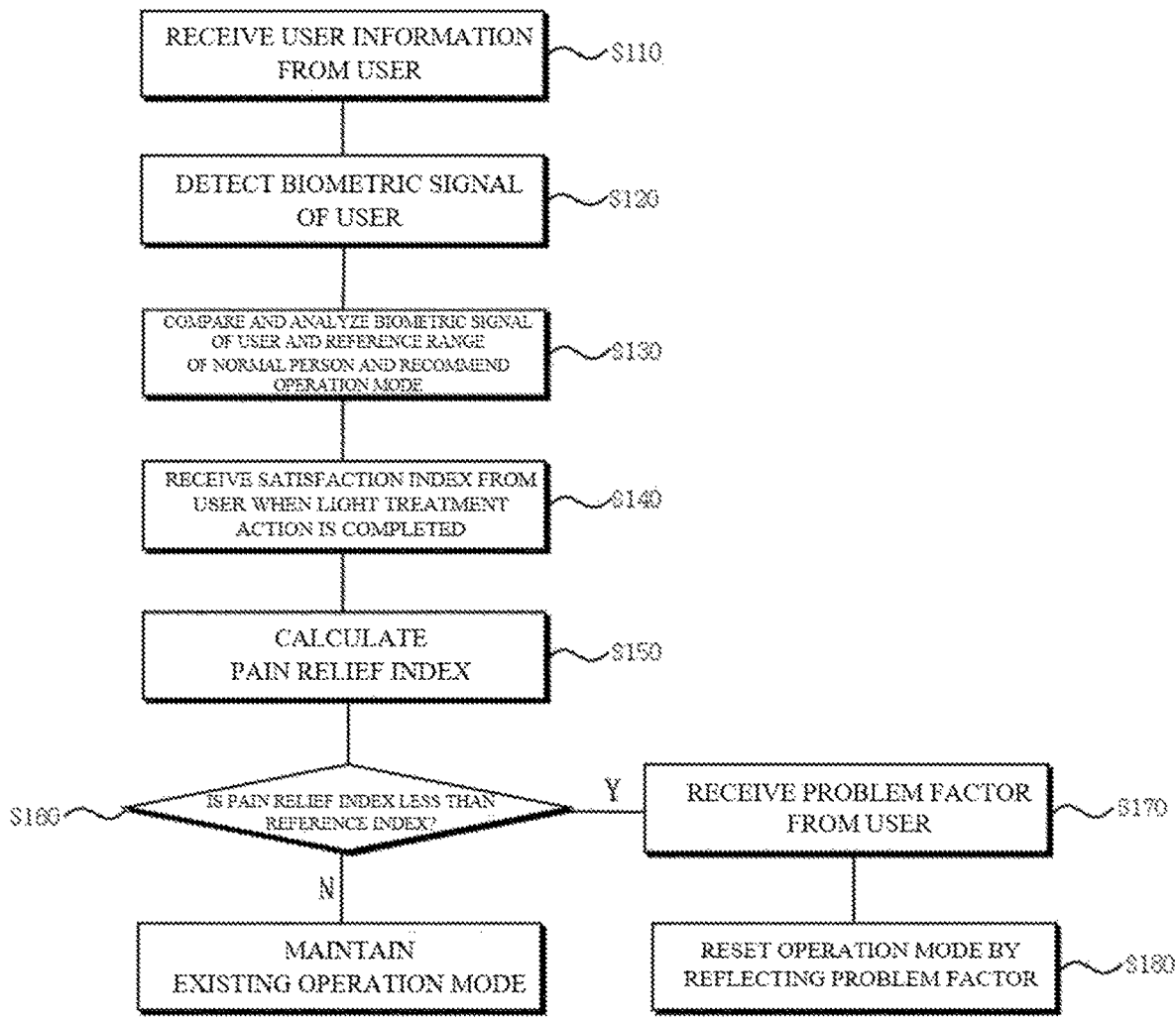
FIG. 7 is a flowchart illustrating a method of controlling the body-wearable apparatus for treating pain by a principle of complex photo-biochemical actions according to one embodiment of the present invention.

As shown in FIGS. 4 and 5, the built-in battery 124 may be formed inside the body portion 110. The built-in battery 124 is charged by a cradle 150 or a charger and may supply power for a light treatment.

The body portion 110 may include a battery housing 126 configured to accommodate and protect the built-in battery 124. The battery housing 126 may include a protrusion on one side thereof.

More specifically, the protrusion may form a predetermined clearance to prevent a short circuit that may occur between the circuit board 122 and the built-in battery 124.

Further, the protrusion may press a heating element 132 such that the heating element 132 is pressed against an inner surface of a treatment-performing-surface side of the body portion 110. Accordingly, heat of the heating element 132 may be more effectively transmitted toward the treatment-performing-surface side of the body portion 110.

Further, since the heating element 132 is located on an end surface of the protrusion, a deterioration phenomenon that may occur when the heating element 132 and the built-in battery 124 come into contact with each other may be prevented.

The circuit board 122 may be mounted inside the body portion 110 so as to correspond to positions of the transmission holes.

The first light irradiating portion 111 may be electrically connected to the circuit board 122 and irradiate LED light through the transmission holes of the body portion 110.

Further, the second light irradiating portion 113 may be electrically connected to the circuit board 122 to irradiate the LED light through the transmission hole of the body portion 110. The second light irradiating portion 113 may include first elements 114, second elements 116, and a third element 118.

According to the present embodiment, as a light treatment is applied by the body-wearable apparatus 100 for treating pain by a principle of complex photo-biochemical actions, photo-biochemical reactions such as cell activation, cell regeneration, cell division, blood flow improvement, vasodilation, cell degradation, nerve stimulation, pain relief, and blood flow enhancement may occur in the treatment site.

The photo-biochemical reactions may occur by irradiating LED light and a low-level laser of a specific wavelength band to the treatment site.

In this case, as the first light irradiating portion 110 irradiates light of a blue LED 112 having a wavelength range of 440 nm to 460 nm to the treatment site, pain perceived by the user may be relieved and a natural recovery force may be increased. As an example, the blue LED 112 may include at least one blue LED element having a specific wavelength of 453 nm. A blue LED light source having a wavelength of 453 nm has a critical significance of promoting the generation and circulation of nitric oxide (NO) when it irradiates light to the body as compared to a blue LED light source of other wavelength bands, thereby improving the supply of oxygen and nutrients to muscles and simultaneously reducing pain transmission. Accordingly, the muscles may be relaxed and the pain may be relieved. In particular, the nitric oxide (NO) has been clinically proven to exhibit antioxidant, cell protection, and anti-inflammatory properties, and may protect muscles and nerves from damage and help prevent further injuries.

Each of the first elements 114 irradiates a low-level laser having a wavelength range of 630 nm to 680 nm to the treatment site, thereby more effectively relieving pain perceived by the user. As an example, the first element 114 may include a low-level laser element that emits a laser having a wavelength of about 650 nm to 660 nm. The first element 114 described above may amplify the production of ATP cells in mitochondria in a protein cell so that a photo-biochemical principle for replacing damaged cells having a pain-inducing factor is exhibited as an activation principle of normal cell regeneration.

Each of the second elements 116 irradiates a low-level laser having a wavelength range of 800 nm to 850 nm to the treatment site, thereby improving blood flow and causing cell regeneration or cell activation of the treatment site. As an example, the second element 116 may include a low-level laser element that emits a laser having a wavelength of 820 nm to 840 nm. The second element 116 causes capillaries to expand to accelerate blood flow, thereby exhibiting an effect of improving blood flow.

The third element 118 irradiates a low-level laser having a wavelength range of 900 nm to 990 nm to the treatment site to stimulate nerves in the treatment site, thereby treating pain. As an example, the second element 116 may include a low-level laser element that emits a laser having a wavelength of about 903 nm to 930 nm, which is known to exhibit a pain-relieving effect by a nerve stimulation principle.

More specifically, as shown in FIGS. 3 and 4, at least two elements of the first element 114 to the third element 118 may operate simultaneously. Since two or more elements simultaneously irradiate low-level lasers to the treatment site to cause complex photo-biochemical reactions, the treatment effect on the treatment site may be increased further.

In addition, the second elements 116 and the third element 118 may be arranged in a central region 30 of the body portion 110, and the first elements 114 and the blue LED 112 may be arranged in a peripheral region 20 of the body portion 110.

In this case, the second elements 116 may be disposed to be spaced apart from both sides of the third element 118, and the first elements 114 may be arranged to surround the central region 30, and the LED elements may be arranged in the peripheral region 20 to surround the first elements 114.

By arranging the laser elements in such a structure, the third element 118 is located on a blood vessel of the user to promote or improve the flow of a specific blood flow, and the remaining first elements 114 and the second elements 116 may more effectively treat pain by irradiating light to the treatment site in a relatively large region.

Meanwhile, as shown in FIGS. 3 and 4, the body portion 110 may further include a heating portion 130 configured to provide thermal energy to the treatment site for thermal treatment, and the heating portion 130 may include a heat sink 134 configured to absorb heat from the second light irradiating portion, the heating element 132 configured to heat the heat sink 134, a temperature sensor configured to sense a temperature of the heat sink 134, and a controller configured to control the heating element 132 according to the temperature of the heat sink 134 by detecting a temperature signal from the temperature sensor.

The heating portion 130 provides thermal energy to the treatment site to expand a blood vessel of the user, improve blood flow, and promote blood circulation, thereby aiding in pain relief.

Here, the heating portion 130 is designed to be heated by the heating element 132 to directly provide thermal energy to the treatment site and may transmit heat generated from the first light irradiating portion 111 and the second light irradiating portion 113 to the heat sink to indirectly transmit additional heat to the treatment site and surrounding portions thereof.

As shown in FIG. 4, in order to more efficiently transmit heat, the heating element 132 may be designed to be in contact with the heat sink, but the heating element 132 may be designed not to be in contact with the heat sink 134.

In addition, in order to control the operation mode of the light irradiating portion, the body portion 110 may further include a biometric signal detection sensor 120 installed therein and configured to detect a biometric signal of the user.

In this case, the biometric signal detection sensor 120 may measure electromyogram, electrocardiogram, ballistocardiogram, seismocardiogram, and photoplethysmogram. It is possible to suggest an optimal treatment method for pain perceived by an individual by detecting the biometric signal of the user and quantifying the pain by the biometric signal detection sensor 120.

In addition, the body portion 110 may include an oscillator 121 therein to apply vibration energy to the treatment site. As the vibration energy is transmitted to the treatment site at the same time as the light treatment, muscles may be relaxed to relieve pain.

Hereinafter, a method of controlling the body-wearable apparatus 100 for treating pain by a principle of complex photo-biochemical actions according to the present invention will be described.

First, user information including body information and indication may be received from a user through a user terminal (S110).

In this case, the body information includes at least one of gender, age, height, and weight, and the indication information may include at least one of a type of indication the user is suffering from, a pain site, and a cause and a symptom of the pain.

As described above, since the user information is collected as a database, a server may provide operation mode information optimized to a user's body condition and state.

After the user information is collected from the user, a biometric signal of the user may be detected through a biometric signal detection sensor 120 (S120), and this biometric signal and the user information described above are comprehensively considered so that an operation mode of each of light irradiating portions 111 and 113 may be recommended (S130).

In the database of the server, biometric signal data of a normal person may be stored. Accordingly, the server may compare and analyze the detected biometric signal with the normal person's biometric signal having body information corresponding to the user. That is, the server may compare the user's biometric signal with a reference range of the normal person to set any one of a plurality of modes as the operation mode, and output the set operation mode to a display of the user terminal.

For example, the biometric signal detection sensor 120 may detect a surface electromyogram signal of the user.

An electromyogram is a biometric signal in which tension generated in a muscle, which is overworked due to excessive exercise or fatigued due to a chronic disease, is detected as an electrical signal and may represent pain caused by musculoskeletal disorders as accurate and objective numerical values.

When voltage or current of the treatment site is detected by the biometric signal detection sensor 120, the server may calculate an effective value for detecting a representative value of an electromyogram signal frequency.

In another example, the biometric signal detection sensor 120 may be attached to the skin to simultaneously measure electrocardiogram, ballistocardiogram, and seismocardiogram.

The ballistocardiogram is an electrical record of vibrations according to a heartbeat, which is generated by the rise and fall of blood flow when blood is released into the aorta by the contraction of heart, and represents the momentum of blood ejected by the heart.

The electrocardiogram is a recording of an activity current, which is generated in a heart muscle according to the beating of a heart, using an ammeter.

The seismocardiogram is a signal reflecting a physical activity of a cardiovascular system according to a blood flow/blood pressure, contraction/relaxation of a heart, and the like rather than an electrical signal of the heart.

The server may detect and store the biometric signal using at least one biometric signal detection sensor 120, analyze the detected signal to extract as a specific point, and calculate cardiovascular parameters using the extracted specific point.

More specifically, the server may extract, as the specific point, a point where a slope of the biometric signal is zero and derive at least one of an isovolumic contraction time (ICT), an isovolumic relaxation time (IRT), a left ventricular ejection time (LVET), a pre-ejection period (PEP), and myocardial perfusion imaging (MP1) from the position, interval, amplitude, and frequency of the extracted specific point as the cardiovascular parameters.

When the calculation of the cardiovascular parameters is completed, the server may output the cardiovascular parameters to the user terminal.

More specifically, the plurality of modes may include first to third modes, and the light irradiating portion may include an LED element configured to emit LED light, and a first element 114, a second element 116, and a third element 118, each of which is configured to emit low-level laser light.

When the biometric signal is less than the reference range, the first mode, in which a blue LED 112 and the first element 114 operate, may be set as the operation mode.

When the biometric signal corresponds to the reference range, the second mode, in which the first element 114 and the second element 116 operate, may be set as the operation mode.

When the biometric signal exceeds the reference range, the third mode, in which the second element 116 and the third element 118 operate, may be set as the operation mode.

When the light irradiating portion operates in the second and third modes, a vibrator operates so that vibration energy is provided to the treatment site, and the vibrator may generate the vibration energy, in which at least one of a vibration period and a vibration intensity is different, in the second and third modes.

When the operation mode is recommended as described above, the user may put the body-wearable apparatus 100 for treating pain by a principle of complex photo-biochemical actions on the treatment site and operate the body-wearable apparatus 100 by setting the operation mode and a treatment time.

Thereafter, when a light treatment is completed, the server may receive a satisfaction index for the light treatment from the user through the user terminal (S140). In this case, the server may confirm a change value of the biometric signal of the user before and after the light treatment by continuously monitoring the biometric signal of the user using the biometric signal detection sensor 120.

Accordingly, the server may analyze the biometric signal of the user and the satisfaction index to calculate a pain relief index (S150).

More specifically, the pain relief index may be calculated by adding an addition index according to the biometric signal to the satisfaction index, which is input by the user, when the biometric signal exceeds the reference value, and the pain relief index may be calculated as the satisfaction index itself when the biometric signal is less than or equal to the reference value.

When the pain relief index is greater than or equal to the reference index, the server may maintain the operation mode of the light irradiating portion (S160).

On the other hand, when the pain relief index is less than the reference index, the server may receive a problem factor from the user and may reset the operation mode of the light irradiating portion according to the problem factor (S160 and S170).

In this case, the problem factor may include at least one of an intensity of the light irradiating portion and the treatment site.

When the problem factor is the intensity of the light irradiating portion, the server may reset the operation mode so that at least one of an operation time and an output of the light irradiating portion is increased.

When the problem factor is the treatment site of the light irradiating portion, the server may adjust the treatment site of the light irradiating portion according to the user information including at least one of height, weight, age, and gender of the user, thereby resetting the operation mode.

More specifically, acupuncture point information of a human body may be stored in the database. The treatment site may be reset as an acupuncture point located at a peripheral portion of a pain portion is reset according to the pain portion that is input to the user information.

As described above, when the operation mode of the light irradiating portion is reset according to the problem factor, the reset operation mode is output to the user terminal, thereby providing feedback about the problem factor re-input by the user.

On the other hand, a body-wearable apparatus 100 for treating pain by a principle of complex photo-biochemical actions according to another embodiment of the present invention will be described with reference to FIGS. 8 and 9.

In the case of the body-wearable apparatus 100 for treating pain by a principle of complex photo-biochemical actions according to the present embodiment, there is a difference from the above-described embodiment in that an ultrasonic element is disposed in a central region, and thus, hereinafter, the present embodiment will be described focusing on an ultrasonic element 119 that is different from the above-described embodiment.

Figure 8:
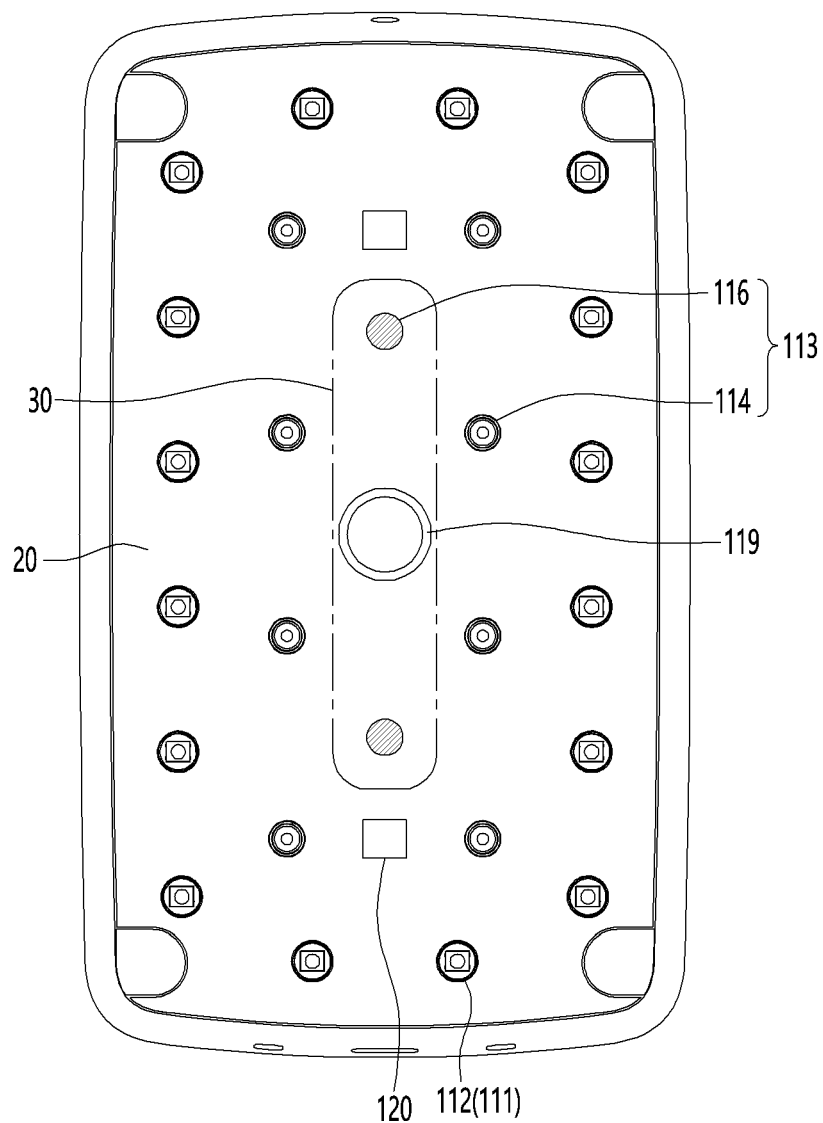
FIG. 8 is a rear view illustrating a body-wearable apparatus for treating pain by a principle of complex photo-biochemical actions according to another embodiment of the present invention.
Figure 9:
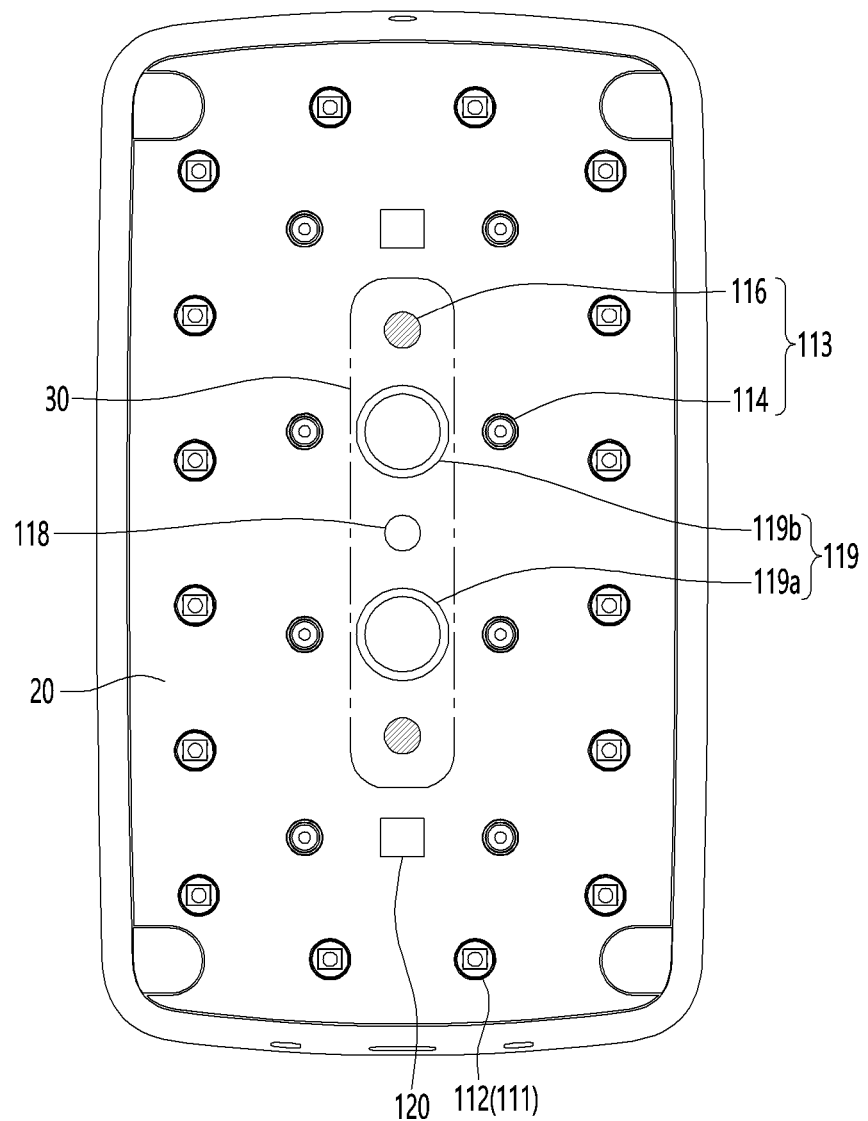
FIG. 9 is a rear view illustrating a body-wearable apparatus for treating pain by a principle of complex photo-biochemical actions according to still another embodiment of the present invention.

As shown in FIG. 8, a body portion may further include the ultrasonic element 119.

In addition, second elements 116 and the ultrasonic element 119 may be disposed in a central region 30 of the body portion.

The ultrasonic element 119 may simultaneously or alternately irradiate a plurality of ultrasonic waves having different frequencies to a treatment site.

For example, the ultrasonic element 119 may alternately generate ultrasonic energy of 1 MHz and 3 MHz. For example, the ultrasonic element 119 may irradiate the ultrasonic energy to the treatment site while modulating the frequency at intervals of three seconds.

As the ultrasonic element 119 irradiates the ultrasonic energy of a frequency of 1 MHz to the treatment site, it is possible to perform treatment by stimulating a deep muscle at a depth of 1 cm to 5 cm from a treatment-performing-surface, and as the ultrasonic element 119 irradiates the ultrasonic energy of a frequency of 3 MHz to the treatment site, it is possible to perform treatment by stimulating a superficial muscle at a depth of 0.7 cm from the treatment-performing-surface.

The ultrasonic element 119 described above may be formed to be thin and small in size so as to be installed inside a small device having a relatively small size.

Further, a body-wearable apparatus 100 for treating pain by a principle of complex photo-biochemical actions according to still another embodiment of the present invention will be described with reference to FIG. 9.

According to the present embodiment, second elements 116, a third element 118, and a plurality of ultrasonic elements 119 may be disposed in a central region 30 of a body portion. The ultrasonic elements 119 include a first ultrasonic element 119a and a second ultrasonic element 119b, and the first and second ultrasonic elements 119a and 119b may irradiate ultrasonic energy of different frequencies. For example, one of the first and second ultrasonic elements 119a and 119b may be an ultrasonic element having a frequency of 1 MHz, and the other one may be an ultrasonic element having a frequency of 3 MHz. As another example, the first and second ultrasonic elements 119a and 119b may be elements capable of irradiating 1 MHz and/or 3 MHz. In this case, the ultrasonic elements 119 independently control each of the first and second ultrasonic elements 119a and 119b to simultaneously emit 1 MHz or 3 MHz to a human body or alternately emit 1 MHz and 3 MHz to the human body. 1 MHz of the first ultrasonic element 119a is used for treatment of deep muscle located at a depth of about 20 mm to 40 mm from a skin surface, and 3 MHz of the second ultrasonic element 119b may be used for treatment of superficial muscle located at a depth of about 1 mm from the skin surface. As described above, the ultrasonic element 119 may be provided to enable effective pain treatment by applying ultrasonic energy so as to simultaneously and/or alternately treat the superficial muscle and the deep muscle in a pain region. The ultrasonic elements 119 may be disposed to be spaced apart from both sides of the third element 118 to transmit ultrasonic energy to a large region.

As described above, since a low-level laser and ultrasonic energy that are effective in pain relief and blood flow improvement are complexly irradiated on a treatment site, a treatment effect on a pain site may be further increased so that a user may perform continuous pain treatment and reduce treatment costs even when the user does not directly visit a hospital.

The embodiments of the present invention have been described above. However, it should be noted that those skilled in the art and understanding the present invention may easily suggest other embodiments by addition, modification, and removal of the components within the same spirit, but these are construed as being included in the spirit of the present invention.

The invention claimed is:

1. A body-wearable apparatus for treating pain by a principle of complex photo-biochemical actions, the apparatus comprising:
a body portion in which a plurality of transmission holes are formed so that light is transmitted therethrough;
a circuit board disposed inside the body portion;
a built-in battery disposed inside the body portion;
a first light irradiating portion electrically connected to the circuit board and configured to irradiate blue light-emitting diode (LED) light through the transmission holes of the body portion; and
a second light irradiating portion electrically connected to the circuit board and configured to irradiate low-level laser light through the transmission holes of the body portion,
wherein each of the first and second light irradiating portions is provided to cause at least two or more photo-biochemical reactions among cell activation, cell regeneration, cell division, blood flow improvement, vasodilation, cell degradation, and nerve stimulation on tissue in a body part to be treated through simultaneous or alternate light output,
wherein the first light irradiating portion comprises a plurality of blue LED elements irradiating the blue LED light having a wavelength range of 440 nm to 460 nm,
wherein the second light irradiating portion comprises:
a plurality of first elements irradiating low-level laser light having a wavelength range of 630 nm to 680 nm for cell regeneration;
a plurality of second elements irradiating low-level laser light having a wavelength range of 800 nm to 850 nm for blood flow improvement; and
a third element disposed in a central region of the body portion and irradiating low-level laser light having a wavelength range of 900 nm to 920 nm for treating pain by nerve stimulation,
wherein the plurality of second elements are disposed in the central region of the body portion and disposed adjacent to the third element,
wherein the plurality of first elements are disposed in a peripheral region of the body portion around the central region of the body portion,
wherein the plurality of blue LED elements are disposed in the peripheral region of the body portion around the plurality of the first elements,
wherein the plurality of the first elements, the plurality of second elements, and the third element operate with the plurality of blue LED elements simultaneously,
wherein the plurality of the second elements disposed adjacent to the third element irradiate the low-level laser light having the wavelength range of 800 nm to 850 nm to a periphery of a nerve to which a light treatment by the third element is applied, so as to contribute to treating the pain by improving blood flow through causing vessels to expand to accelerate blood flow,
wherein the plurality of the first elements disposed around the third element and the plurality of the second elements irradiate the low-level laser light having the wavelength range of 630 nm to 680 nm to a periphery of the nerve to which the light treatment by the third element is applied and of the vessels to which a light treatment by the plurality of second elements is applied, so as to contribute to treating the pain by activating normal cell regeneration through amplifying a production of ATP cells in mitochondria in a protein cell, and
wherein the plurality of blue LED elements disposed around the plurality of the first elements irradiate the blue LED light having the wavelength range of 440 nm to 460 nm to a periphery of tissue to which the light treatment by the plurality of first elements, the plurality of second elements, and the third element are applied, so as to contribute to treating the pain by improving supply of oxygen and nutrients to muscles and reducing pain transmission through promoting generation and circulation of nitric oxide (NO).

2. The apparatus of claim 1, further comprising an ultrasonic element provided in the body portion and controlled to simultaneously or alternately generate at least one ultrasonic energy of 1 MHz and 3 MHz toward a body,
wherein the first light irradiating portion, the second light irradiating portion, and the ultrasonic element simultaneously emit light.

3. The apparatus of claim 2, wherein
the body portion further includes a heating portion configured to provide thermal energy to a treatment site for thermal treatment,
wherein the heating portion includes a heat sink provided to absorb heat from the second light irradiating portion, a heating element configured to heat the heat sink, a temperature sensor configured to sense a temperature of the heat sink, and a controller configured to control the heating element according to the temperature of the heat sink by detecting a temperature signal from the temperature sensor.

4. The apparatus of claim 2, further comprising a biometric signal detection sensor installed in the body portion and configured to detect a biometric signal of a user in order to control an operation mode of the first and second light irradiating portions.

5. The apparatus of claim 1, further comprising an ultrasonic element provided in the body portion and controlled to simultaneously or alternately generate ultrasonic energy for treatment of superficial muscle and ultrasonic energy for treatment of deep muscle,
wherein the first light irradiating portion, the second light irradiating portion, and the ultrasonic element simultaneously emit light.

6. The apparatus of claim 5, wherein
the body portion further includes a heating portion configured to provide thermal energy to a treatment site for thermal treatment,
wherein the heating portion includes a heat sink provided to absorb heat from the second light irradiating portion, a heating element configured to heat the heat sink, a temperature sensor configured to sense a temperature of the heat sink, and a controller configured to control the heating element according to the temperature of the heat sink by detecting a temperature signal from the temperature sensor.

7. The apparatus of claim 5, further comprising a biometric signal detection sensor installed in the body portion and configured to detect a biometric signal of a user in order to control an operation mode of the first and second light irradiating portions.

8. The apparatus of claim 1, wherein
the body portion further includes a heating portion configured to provide thermal energy to a treatment site for thermal treatment,
wherein the heating portion includes a heat sink provided to absorb heat from the second light irradiating portion, a heating element configured to heat the heat sink, a temperature sensor configured to sense a temperature of the heat sink, and a controller configured to control the heating element according to the temperature of the heat sink by detecting a temperature signal from the temperature sensor.

9. The apparatus of claim 1, further comprising a biometric signal detection sensor installed in the body portion and configured to detect a biometric signal of a user in order to control an operation mode of the first and second light irradiating portions.

10. The apparatus of claim 1, wherein
the body portion further includes a heating portion configured to provide thermal energy to a treatment site for thermal treatment,
wherein the heating portion includes a heat sink provided to absorb heat from the second light irradiating portion, a heating element configured to heat the heat sink, a temperature sensor configured to sense a temperature of the heat sink, and a controller configured to control the heating element according to the temperature of the heat sink by detecting a temperature signal from the temperature sensor.

* * * * *